United States Patent
Kono et al.

(10) Patent No.: US 10,227,062 B2
(45) Date of Patent: Mar. 12, 2019

(54) LIQUID-DROPLET DETECTING APPARATUS, LIQUID-DROPLET DETECTING METHOD, AND COMPUTER-READABLE RECORDING MEDIUM

(71) Applicant: FUJITSU TEN LIMITED, Kobe-shi, Hyogo (JP)

(72) Inventors: Takashi Kono, Kobe (JP); Junji Hashimoto, Kobe (JP); Yasushi Tani, Kobe (JP); Tomohide Kasame, Kobe (JP); Teruhiko Kamibayashi, Kobe (JP); Hiroki Murasumi, Kobe (JP)

(73) Assignee: FUJITSU TEN LIMITED, Kobe-shi (JP)

( * ) Notice: Subject to any disclaimer, the term of this patent is extended or adjusted under 35 U.S.C. 154(b) by 0 days.

(21) Appl. No.: 15/670,617

(22) Filed: Aug. 7, 2017

(65) Prior Publication Data

US 2018/0086309 A1    Mar. 29, 2018

(30) Foreign Application Priority Data

Sep. 23, 2016  (JP) ................................. 2016-186245

(51) Int. Cl.
*B60S 1/08* (2006.01)
*G01N 21/958* (2006.01)
*G06T 7/12* (2017.01)

(52) U.S. Cl.
CPC .......... *B60S 1/0844* (2013.01); *G01N 21/958* (2013.01); *G06T 7/12* (2017.01)

(58) Field of Classification Search
CPC ........................... G01N 21/958; B60S 1/0844
USPC ......................................................... 382/103
See application file for complete search history.

(56) References Cited

U.S. PATENT DOCUMENTS 8,654,427 B1 * 2/2014 DeAngelo .............. G02B 7/004
359/221.2

FOREIGN PATENT DOCUMENTS

| JP | 2010-014494 A |   | 1/2010 |             |
|----|---------------|---|--------|-------------|
| JP | 2010014494 A  | * | 1/2010 | G01N 21/17  |
| JP | 2010014494 A  | * | 1/2010 | G01N 21/17  |

* cited by examiner

*Primary Examiner* — Gregory F Cunningham
(74) *Attorney, Agent, or Firm* — Oliff PLC

(57) ABSTRACT

A water-droplet detecting apparatus according to an embodiment includes a setting unit, a first extraction unit, a second extraction unit, and a determination unit. The setting unit sets concentric circles having a center at arbitrary one point of a captured image of an image capturing unit. The first extraction unit extracts candidate pixels based on gradients of pixels on a circumference of each of the concentric circles. The candidate pixels are candidates for pixels that are estimated to indicate a water droplet adhered to the image capturing unit. The second extraction unit extracts one or more candidate circles based on the candidate pixels extracted by the first extraction unit. The one or more candidate circles are candidates for circles that indicate a shape of the water droplet. The determination unit determines whether or not the water droplet is adhered based on an extraction result of the second extraction unit.

20 Claims, 10 Drawing Sheets

DISTRIBUTION PATTERN

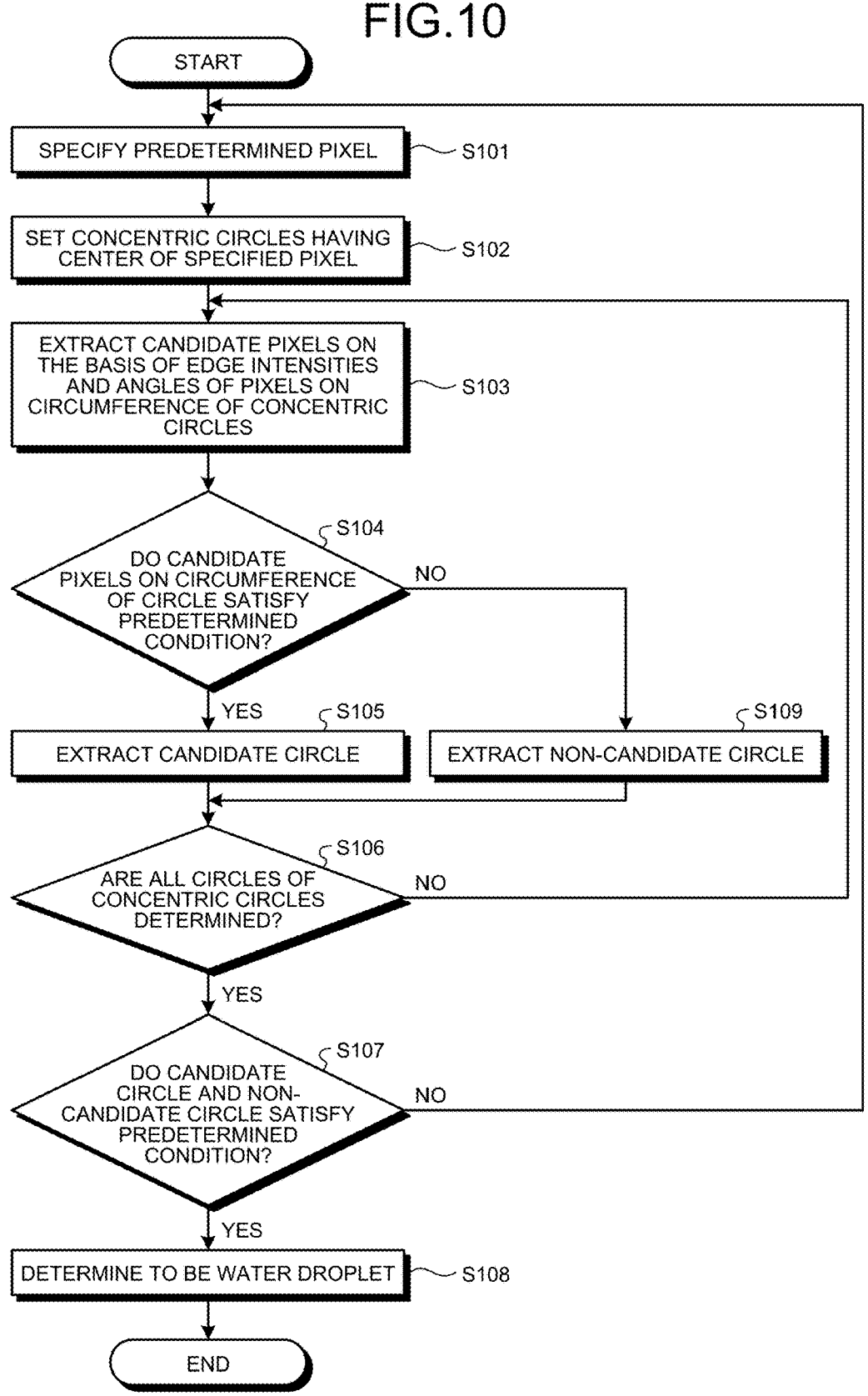

LIQUID-DROPLET DETECTING APPARATUS, LIQUID-DROPLET DETECTING METHOD, AND COMPUTER-READABLE RECORDING MEDIUM

CROSS-REFERENCE TO RELATED APPLICATION

This application is based upon and claims the benefit of priority of the prior Japanese Patent Application No. 2016-186245, filed on Sep. 23, 2016, the entire contents of which are incorporated herein by reference.

FIELD

The embodiment discussed herein is directed to a water-droplet detecting apparatus, a water-droplet detecting method, and a computer-readable recording medium.

BACKGROUND

There is known a water-droplet detecting apparatus that detects a water droplet such as a raindrop adhered to a lens of a camera attached to a vehicle. For example, the water-droplet detecting apparatus detects the adhesion of the water droplet on the basis of a gradient of each pixel of a captured image (see Japanese Laid-open Patent Publication No. 2010-014494, for example).

However, the conventional technology is needed to detect the gradients of all of the pixels of the captured image, and thus there exists a fear that a processing load is large. Moreover, narrowing down a region to be detected from a whole of the captured image is difficult, and thus the water droplet is not always detected with high accuracy.

SUMMARY

A water-droplet detecting apparatus according to an embodiment includes a setting unit, a first extraction unit, a second extraction unit, and a determination unit. The setting unit sets concentric circles having a center at arbitrary one point of a captured image of an image capturing unit. The first extraction unit extracts candidate pixels on the basis of gradients of pixels on a circumference of each of the concentric circles set by the setting unit. The candidate pixels are candidates for pixels that are estimated to indicate a water droplet adhered to the image capturing unit. The second extraction unit extracts one or more candidate circles on the basis of the candidate pixels extracted by the first extraction unit. The one or more candidate circles are candidates for circles that indicate a shape of the water droplet. The determination unit determines whether or not the water droplet is adhered on the basis of an extraction result of the second extraction unit.

BRIEF DESCRIPTION OF DRAWINGS

A more complete appreciation of the disclosed technology and many of the attendant advantages thereof will be readily obtained as the same becomes better understood by reference to the following detailed description when considered in connection with the accompanying drawings, wherein:

FIG. 10 is a flowchart illustrating a processing procedure of a detection process to be executed by the water-droplet detecting apparatus according to the embodiment.

DESCRIPTION OF EMBODIMENT

Hereinafter, an embodiment of a water-droplet detecting apparatus, a water-droplet detecting method, and a computer-readable recording medium disclosed in the present application will be described in detail with reference to the accompanying drawings. Moreover, the embodiment described below is merely one example, and not intended to limit the present disclosure. It is not intended that the present disclosure be limited to the embodiment described below. Hereinafter, a case will be explained as an example, in which a water droplet adhered to a lens of an on-vehicle camera (hereinafter, may be referred to as "camera"), namely an image capturing unit, is detected.

The above water droplet includes, for example, a raindrop directly coming to adhere to a lens caused by the rainfall, a raindrop caused by the rainfall streaming along a vehicle body so as to indirectly come to adhere to a lens, muddy water splashed by a tire of a running vehicle, washer fluid for windows of a vehicle or a lens of a camera, and the like.

Figure 1A:
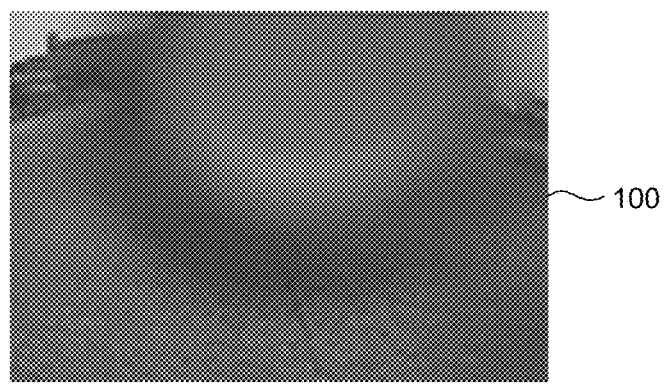
FIGS. 1A to 1C are diagrams illustrating an outline of a water-droplet detecting method according to an embodiment.
Figure 1B:
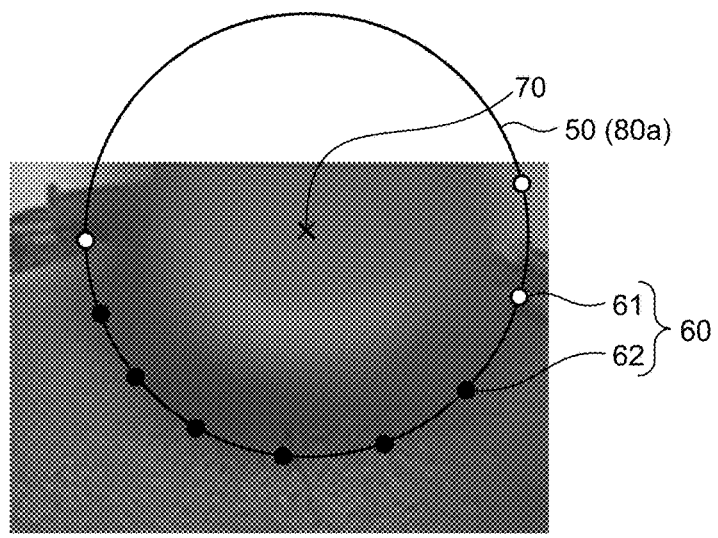
Figure 1C:
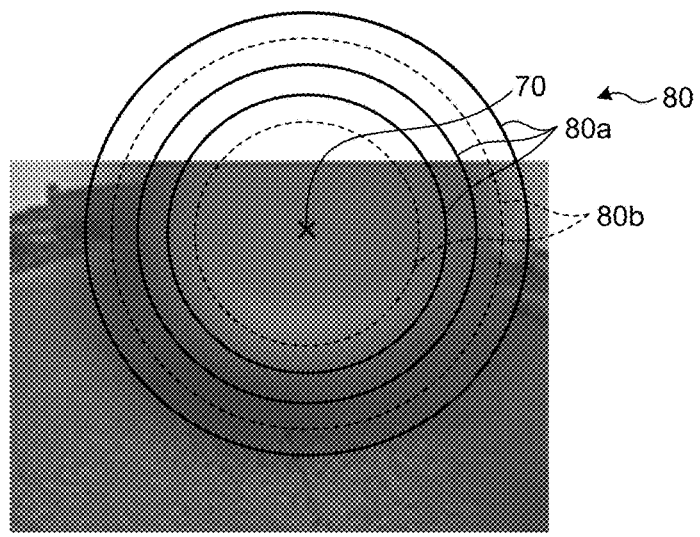

First, an outline of a water-droplet detecting method according to the embodiment will be explained with reference to FIGS. 1A to 1C. FIGS. 1A to 1C are diagrams illustrating the outline of the water-droplet detecting method according to the embodiment. In FIGS. 1A to 1C, a captured image 100 is illustrated, which is acquired by the water-droplet detecting apparatus executing the water-droplet detecting method according to the embodiment.

As illustrated in FIG. 1A, this captured image 100 includes a substantially circle-shaped region (hereinafter, may be referred to as "water-droplet region") indicating a water droplet adhered to a lens of a camera. In the example illustrated in FIG. 1A, the water-droplet region includes a substantially circle-shaped gray-color region blurred in gray and a black-color region that is a substantially circle-shaped part surrounding this gray-color region and blurred in blacker than the gray-color region.

These gray-color and black-color regions are arranged, so to speak, concentrically. This is because a water droplet tends to easily adhere to the lens in semispherical three-dimensional shape.

The water-droplet detecting method according to the embodiment focuses on this point so as to extract a circle indicating a shape of a water droplet on the basis of gradients of pixels existing on circumferences of concentric circles set at arbitrary positions of the captured image 100, and detects adhesion of the water droplet on the basis of the extracted circle.

Hereinafter, an intensity of a gradient of a pixel and a direction of the gradient may be referred to as "edge intensity" and "edge direction", respectively.

Herein, a conventional water-droplet detecting method will be explained. In the conventional water-droplet detecting method, an edge detecting process is executed on each pixel of a captured image and a circle indicating a shape of a water droplet is extracted by using gradients of the pixels of a whole of the captured image.

However, in the conventional water-droplet detecting method, the edge detecting process is needed to be executed on all of the pixels of the captured image, and thus there exists a fear that a processing load is large. The gradient of each of the pixels of the whole of captured image includes an edge caused by various objects other than the water droplet, and thus narrowing down a water-droplet region is difficult and the water droplet is hardly detected with high accuracy.

Therefore, in the water-droplet detecting method according to the embodiment, pixels on which the edge detecting process is to be executed are narrowed down on the basis of the above concentric circles. Specifically, as illustrated in FIG. 1B, in the water-droplet detecting method, first, concentric circles 80 (see FIG. 1C) are set, which center a center 70 that is positioned at arbitrary one point in the captured image 100 of the camera (image capturing unit). In FIG. 1B, one circle 50 is illustrated from among a plurality of circles of the concentric circles 80.

Next, as illustrated in FIG. 1B, the water-droplet detecting method extracts, from among pixels 60 on a circumference of each of the set concentric circles 80, candidate pixels 62 that are candidates for pixels estimated to indicate a water droplet adhered to the camera, on the basis of gradients of the pixels 60. The gradients of the pixels 60 can be acquired by an already-known edge-detecting process such as a Sobel filter.

In FIG. 1B, a selected part of the pixels 60 on a circumference of the circle 50 is illustrated, and a process for selecting these pixels 60 is executed in the present embodiment. This process for selecting the pixels 60 will be mentioned later with reference to FIGS. 4A to 4C. In the present embodiment, the pixels 60 not being the candidate pixel 62 are extracted from among the pixels 60 illustrated in FIG. 1B as non-candidate pixels 61, and this point will be also mentioned later.

Next, as illustrated in FIG. 1B, the water-droplet detecting method according to the embodiment extracts, on the basis of the extracted candidate pixels 62, candidate circles 80a that are candidates for circles indicating a shape of the water droplet. For example, in the present embodiment, as illustrated in FIG. 1B, when the number of the candidate pixels 62 on the circumference of the circle 50 is equal to or more than a predetermined number (in FIG. 1B, "6"), the circle 50 is extracted as the candidate circle 80a.

Next, the water-droplet detecting method according to the embodiment determines, on the basis of an extraction result of the candidate circles 80a, whether or not the water droplet is adhered. For example, in the present embodiment, as illustrated in FIG. 1C, when the number of the existing extracted candidate circles 80a is equal to or more than a predetermined number (in FIG. 1C, "3"), a water droplet is determined to be adhered.

Thus, in the water-droplet detecting method according to the embodiment, a shape of a water-droplet region when the water droplet is adhered to a lens is focused on, and the edge detecting process is executed, which narrows down targets into the pixels 60 existing on the circumference of each of the concentric circles 80 having a canter of arbitrary one point in the whole of the captured image 100.

In other words, because the process is executed on each of the concentric circles 80 that are set in accordance with a shape of a water-droplet region, efficiency of the process can be improved. The edge detecting process is executed, whose targets are narrowed down into shapes indicating tendencies toward the water-droplet region, and thus edges to be detected hardly include an edge caused by another object. Therefore, a water droplet can be detected with high accuracy while reducing a processing load.

Figure 2:
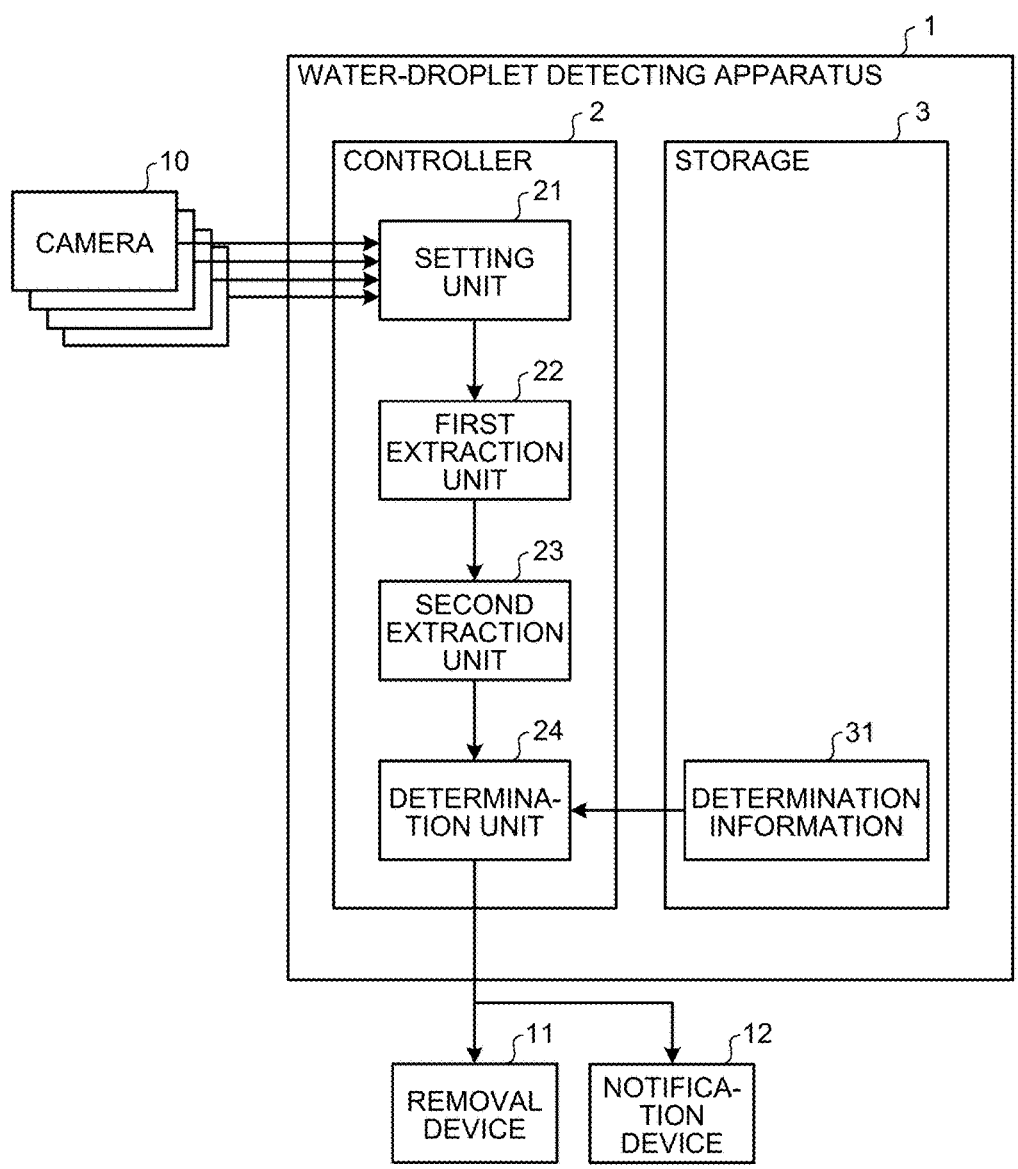
FIG. 2 is a block diagram illustrating a configuration of a water-droplet detecting apparatus according to the embodiment.

Next, with reference to FIG. 2, a configuration of the water-droplet detecting apparatus according to the embodiment will be specifically explained. FIG. 2 is a block diagram illustrating a configuration of a water-droplet detecting apparatus 1 according to the embodiment.

As illustrated in FIG. 2, the water-droplet detecting apparatus 1 is connected with cameras 10, a removal device 11, and a notification device 12. First, a configuration of the devices other than the water-droplet detecting apparatus 1 will be explained.

Each of the four cameras 10 includes image capturing elements such as a Charge Coupled Device (CCD) and a Complementary Metal Oxide Semiconductor (CMOS), and the four cameras 10 are attached to positions from which, for example, the front, back, right, and left of a vehicle are captured, respectively. Each of the cameras 10 outputs the captured images 100 to the water-droplet detecting apparatus 1.

The removal device 11 automatically removes water droplets adhered to the cameras 10 on the basis of a detection result of the water-droplet detecting apparatus 1. The removal device 11 includes, for example, an air compressing unit, hoses, and nozzles, and jets compressed air generated by the air compressing unit toward the cameras 10 from the nozzles through the hoses so as to remove water droplets. However not limited thereto, for example, the removal device 11 may jet washer fluid toward the cameras 10 or camera wipers may wipe the cameras 10.

The notification device 12 includes, for example, a display and a speaker, and is connected with various systems utilizing the captured images 100 of the cameras 10. The notification device 12 notifies a driver of a fact that a function of various systems is to be stopped by using text display and sound, on the basis of a detection result of the water-droplet detecting apparatus 1.

The various systems include an obstacle detecting system that detects an obstacle existing in the vicinity of the vehicle, a white-line detecting system for detecting a running lane, and the like. Not limited thereto, any system using the captured images 100 of the cameras 10 is sufficient.

Next, a configuration of the water-droplet detecting apparatus 1 will be explained. The water-droplet detecting apparatus 1 includes a controller 2 and a storage 3. The controller 2 includes a setting unit 21, a first extraction unit 22, a second extraction unit 23, and a determination unit 24. The storage 3 stores determination information 31.

Herein, the water-droplet detecting apparatus 1 includes a computer including, for example, a Central Processing Unit (CPU), a Read Only Memory (ROM), a Random Access Memory (RAM), a Hard Disk Drive (HDD), an input/output port, etc. and various circuits.

The CPU of the computer reads and executes, for example, a program stored in the ROM so as to function as the setting unit 21, the first extraction unit 22, the second extraction unit 23, and the determination unit 24 of the controller 2.

At least a part or all of the setting unit 21, the first extraction unit 22, the first extraction unit 22, the second extraction unit 23, and the determination unit 24 of the controller 2 may be constituted of hardware such as an Application Specific Integrated Circuit (ASIC) and a Field Programmable Gate Array (FPGA).

The storage 3 corresponds to, for example, the RAM and the HDD. The RAM and the HDD can store the determination information 31 and information on various programs. The water-droplet detecting apparatus 1 may acquire the above programs and various kinds of information through another computer connected by a wired or wireless network, or a portable recording medium.

The setting unit 21 sets the concentric circles 80 having a canter of the center 70 positioned at arbitrary one point in the captured image 100 of the camera 10 (image capturing unit). Specific processing details of the setting unit 21 will be mentioned later with reference to FIGS. 3A to 3F.

The first extraction unit 22 extracts the candidate pixels 62, which are candidates for pixels estimated to indicate a water droplet adhered to a lens of the camera 10 (image capturing unit), on the basis of gradients of the pixels 60 existing on a circumference of each of the concentric circles 80 set by the setting unit 21. Specific processing details of the first extraction unit 22 will be mentioned later with reference to FIGS. 4A to 5B.

The second extraction unit 23 extracts the candidate circles 80a, which are candidates for circles indicating a shape of a water droplet, on the basis of the candidate pixels 62 extracted by the first extraction unit 22. Specific processing details of the second extraction unit 23 will be mentioned later with reference to FIGS. 6A to 6C.

The determination unit 24 determines whether or not the water droplet is adhered on the basis of the extraction result of the second extraction unit 23. Specific processing details of the determination unit 24 will be mentioned later with reference to FIGS. 7 to 9.

Next, with reference to FIGS. 3A to 3F, processing details of the setting unit 21 will be specifically explained. FIGS. 3A to 3F are diagrams illustrating processes for setting the concentric circles 80 to be executed by the setting unit 21. As described above, the setting unit 21 sets the concentric circles 80 whose canter is the center 70 positioned at arbitrary one point in the captured image 100 of the camera 10.

Figure 3A:
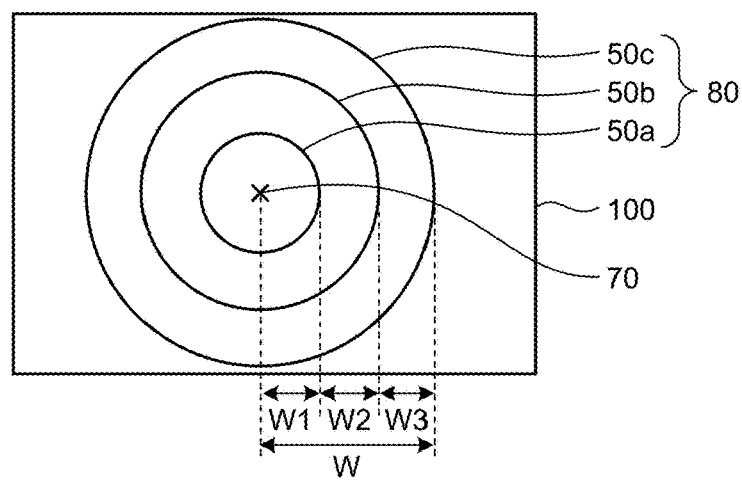
FIGS. 3A to 3F are a diagrams illustrating processes for setting concentric circles to be executed by a setting unit.

Specifically, first, the setting unit 21 specifies an arbitrary pixel from the captured image 100. Next, as illustrated in FIG. 3A, the setting unit 21 sets, from among the concentric circles 80, a circle 50c of a maximum radius W having the center 70 that is the specified pixel. It is preferable that the maximum radius W is slightly larger than a radius of a standard water droplet which is preliminary obtained by, for example, experiments and the like.

Next, for example, the setting unit 21 sets a predetermined number of circles on an inner-peripheral side of the circle 50c. As illustrated in FIG. 3A, the setting unit 21 sets two circles 50a and 50b so that the intervals therebetween are, for example, preliminary-set intervals W1, W2, and W3.

When any of the concentric circles 80 set by the determination unit 24 to be mentioned later is not a water-droplet region, the setting unit 21 sets, for example, an adjacent pixel as the center 70 of the next concentric circles 80, and then sequentially sets pixels of the captured image 100 as the center 70.

The numbers and the intervals W1, W2, and W3 of the respective circles 50a, 50b, and 50c of the concentric circles 80 are not limited to the predetermined, the numbers and the intervals may be dynamically set in accordance with, for example, a running speed of a vehicle.

In FIG. 3A, each of the circles 50a, 50b, and 50c of the concentric circles 80 is illustrated by a perfect circle, however, each of the circles 50a, 50b, and 50c is not limited to a perfect circle and may be an ellipse. In this case, a length of a long axis as the maximum radius of the ellipse and a length of a short axis may be set.

The setting unit 21 sets here the concentric circles 80 having the center 70 that is arbitrary one pixel among all of the pixels of the captured image 100, targets of the centers 70 may be a part of the pixels, and pixels to be the centers 70 may be set in, for example, a specific narrowed region of the captured image 100.

For example, the setting unit 21 may preferentially set the centers 70 in a central region of the captured image 100. Specifically, as illustrated in FIG. 3B, the setting unit 21 has a central region that is a rectangular region having predetermined vertical and lateral lengths.

In other words, the setting unit 21 preferentially set, as targets of the centers 70, a central region that is to be an obstacle in controlling the white-line detecting system and the like when a water droplet is adhered thereto. Thus, a processing load can be reduced while detecting, with high accuracy, a water droplet to be an obstacle to a system control.

Figure 3B:
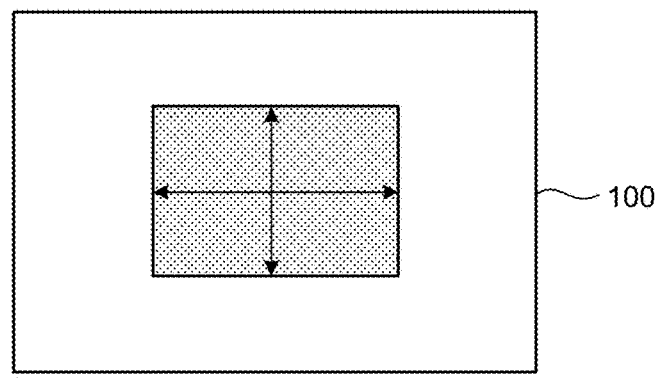

In FIG. 3B, the central region is rectangular-shaped, not limited thereto, the central region may be, for example, circle-shaped having a predetermined radius.

In FIG. 3B, the vertical and lateral lengths of the central region are shorter than respective vertical and lateral lengths of the captured image 100, not limited thereto, for example, only one of the vertical and lateral lengths of the central region may be shorter than the corresponding length of the captured image 100.

The setting unit 21 may decide an area and a position of the central region in accordance with a system connected with the water-droplet detecting apparatus 1. For example, when the water-droplet detecting apparatus 1 is connected with the white-line detecting system, for example, a region corresponding to a position according to a curvature of a curved road may be set as the central region, and the area of this central region is set to be equal to or slightly larger than an corresponding area between white lines existing on the right and left sides of the vehicle.

When the water-droplet detecting apparatus 1 is connected with the obstacle detecting system, the setting unit 21 sets, as the central region, a region corresponding to a periphery of service road such as a sidewalk or a region corresponding to a position of another vehicle running in front which is detected by using, for example, a millimeter-wave radar.

The setting unit 21 sets an adjacent pixel as a pixel to be the next center 70, not limited thereto. For example, as illustrated in FIG. 3C, when moving the concentric circles 80, the setting unit 21 may set, as the new center 70 of the concentric circles 80, a position having an interval by at least one pixel from the center 70 of the concentric circles 80.

Figure 3C:
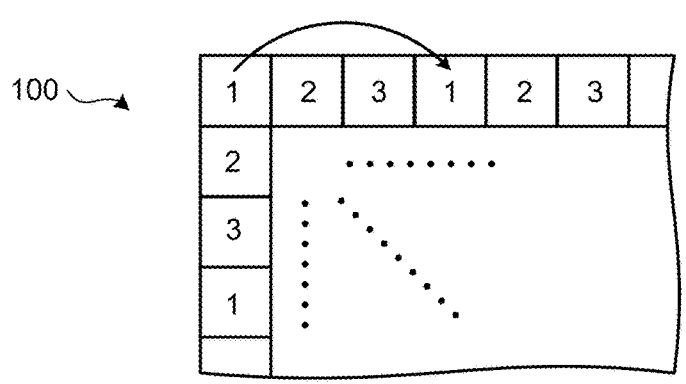

In FIG. 3C, a part of pixels of the captured image 100 is illustrated. In FIG. 3C, for the convenience of explanation, the number is given to each of the pixels, and this number indicates in what round the pixel is set as the center 70.

For example, each of the pixels having the number "1" among the pixels illustrated in FIG. 3C indicates a pixel that is to be set as the center 70 in the first round. The pixels of the centers 70 in the first round have therebetween two-pixel intervals in each of the row and column directions.

Herein, it is assumed that, as illustrated in FIG. 3C, the setting unit 21 sets, from among, for example, first-round pixels, a left-upper-end pixel of the captured image 100 as the center 70, and executes a latter-part process for detecting a water droplet by using the concentric circles 80 of the set center 70.

As illustrated in FIG. 3C, when the latter-part process for detecting a water droplet is completed, the setting unit 21 sets, as the next center 70, a first-round pixel having therefrom a two-pixel interval. When the setting of the centers 70 of the first-round pixels of the captured image 100 is completed, the setting unit 21 sets next second-round pixels as the centers 70.

In other words, the setting unit 21 sets pixels of the centers 70 having therebetween at-least-one-pixel interval so as to give first a priority to scanning a whole of the captured image 100. Therefore, a scanning speed of the captured image 100 can be improved.

In FIG. 3C, the setting unit 21 sets at-least-one-pixel intervals in each of the row and column directions, the setting unit 21 may set at-least-one-pixel intervals in one of the row and column directions.

In FIG. 3C, the setting unit 21 sets pixels to be the centers 70 at equal two-pixel intervals. However the intervals may be variable. For example, the setting unit 21 may set, in the central region (see FIG. 3B), pixels to be the centers 70 whose intervals are shorter than those in other region. Thus, a water droplet existing in the central region can be detected with high accuracy while reducing a processing load.

When a determination process of the determination unit 24 to be mentioned later is completed, the setting unit 21 shifts the process to the next center 70, however, for example, when the determination unit 24 detects a water droplet, the shift to the next center 70 may be stopped.

Specifically, when the determination unit 24 determines that a water droplet is adhered, the setting unit 21 stops setting the center 70 from the frame image. The setting unit 21 shifts the process to the next frame image.

In other words, only one water droplet is detected in one frame image. Thus, if one water droplet can be detected, for example, the removal device 11 can execute a process for removing the water droplet, and thus there exists no need to perform detection of an additional water droplet in the frame, so that it is possible to omit a useless process for detecting a water droplet. Therefore, a processing load can be reduced.

Not limited to the case where the centers 70 are set within the captured image 100, the setting unit 21 may set the centers 70 outside the captured image 100. Specifically, as illustrated in FIG. 3D, the setting unit 21 provides an extension region 101 obtained by extending the captured image 100 toward outer peripheral sides, and enables the center 70 of the concentric circles 80 to be set in the extension region 101.

For example, the setting unit 21 generates, for example, the plain extension region 101 to obtain an image whose size is equal to that of the captured image 100 of predetermined magnifications, and superimposes the captured image 100 on this extension region 101. Thus, a water droplet existing at the edge of the captured image 100 can be detected.

Figure 3D:
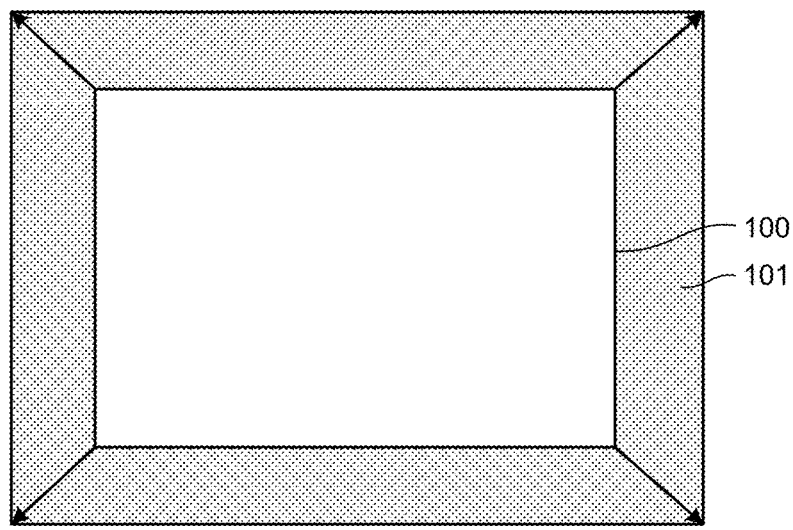

In FIG. 3D, the extension region 101 is provided so as to surround the four sides (upper and lower, and right and left) of the captured image 100, not limited thereto, for example, the extension region 101 may be provided at the two sides (upper and lower, or right and left) of the captured image 100, or one of upper and lower, and the right and left of the captured image 100.

Figure 3E:
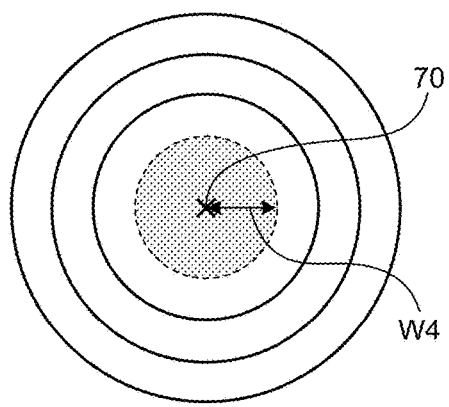

The setting unit 21 may except a specific region in a region having the maximum radius W from a target in which the circles 50a, 50b, and 50c are set. For example, as illustrated in FIG. 3E, the setting unit 21 does not provide the circles 50 of the concentric circles 80 so that a region having a predetermined radius W4 from the center 70 of the concentric circles 80 is not a target for extracting the candidate pixel 62 to be mentioned later.

Herein, the predetermined radius W4 is assumed to be a radius of the gray-color region (see FIG. 1A) preliminary obtained by, for example, experiments and the like. In other words, the setting unit 21 excepts a gray-color region, which substantially uniformly blurs and hardly indicates a tendency toward an edge, from a target for setting the circles 50a, 50b, and 50c. Thus, a processing load can be reduced.

Figure 3F:
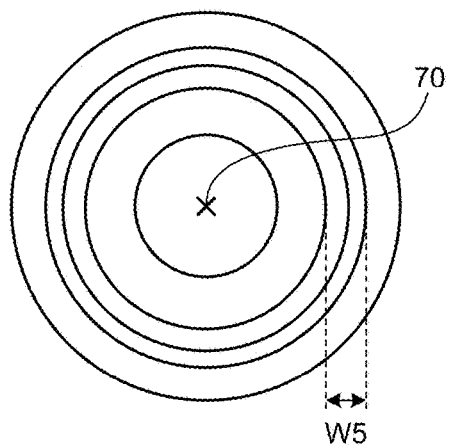

The setting unit 21 may set the predetermined intervals W1, W2, and W3 that are similar to one another, in other words, equal intervals, alternatively, as illustrated in FIG. 3F, the predetermined intervals W1, W2, and W3 may be different from one another. Herein, in FIG. 3F, five circles are illustrated as the concentric circles 80.

For example, as illustrated in FIG. 3F, the setting unit 21 sets an interval, between circumferences of the concentric circles 80 in a predetermined range W5 that is estimated to correspond to an outer periphery of a water droplet, to be shorter than that outside of the predetermined range W5. Herein, the predetermined range W5 is a width of a region to be a boundary between, for example, gray-color and black-color regions (see FIG. 1A).

In other words, the setting unit 21 sets many circles in a boundary region having a tendency toward indication of an edge. Thus, features of edges of a water droplet can be detected more easily, so that it is possible to detect the water droplet with high accuracy. The interval may be set larger than usual in the region other than this boundary region. Thus, a processing load can be reduced.

Figure 4A:
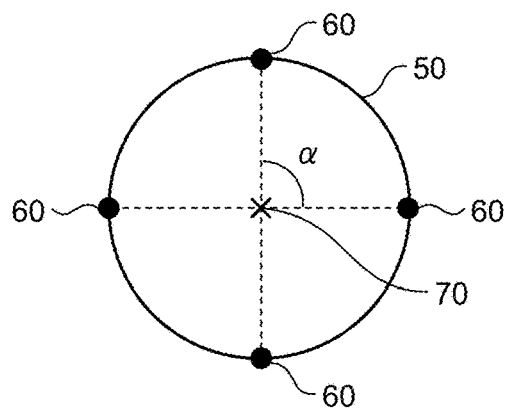
FIGS. 4A to 4C are a diagrams illustrating processes for selecting pixels to be executed by a first extraction unit.
Figure 4B:
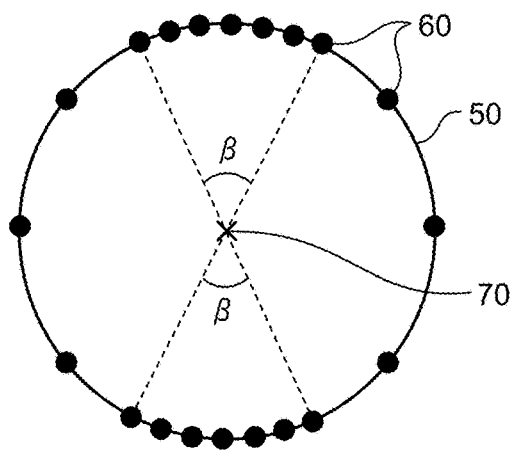
Figure 4C:
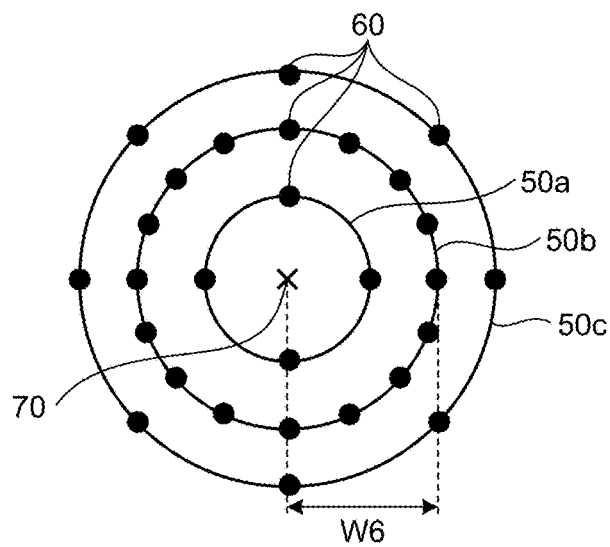

Next, with reference to FIGS. 4A to 4C, a process for selecting the pixels 60 to be executed by the first extraction unit 22 will be explained. FIGS. 4A to 4C are diagrams illustrating processes for selecting the pixels 60 to be executed by the first extraction unit 22. In FIG. 4A, the one circle 50 among the concentric circles 80 is illustrated.

As illustrated in FIG. 4A, the first extraction unit 22 extracts the candidate pixel 62 from among the plurality of pixels 60 that are selected, at predetermined intervals, from a circumference of each of the concentric circles 80 set by the setting unit 21. The first extraction unit 22 selects the pixel 60 from among pixels on the circumference of, for example, the set circle 50 for each predetermined angle α. Thus, the first extraction unit 22 can execute a process for equally extracting the candidate pixel 62 from a whole of the circle 50.

The selection of the pixels 60 performed by the first extraction unit 22 is not limited to that performed at the intervals of the angle α with respect to all of the plurality of circles 50 of the concentric circles 80. For example, the first extraction unit 22 may set intervals, at which the plurality of pixels 60 are selected, to be variable in accordance with a radius of each of the circles 50 of the concentric circles 80.

Specifically, the first extraction unit 22 sets the number of the pixels 60 to be selected to be larger as a radius of the circle 50 is longer. In other words, the angle α is set to be smaller in accordance with a radius of each of the circles 50.

Thus, it can be prevented that a distance between selected pixels is longer as a radius of each of the circles 50 is longer.

Moreover, the first extraction unit 22 is not to equally set all of the intervals between the pixels 60 in the circle 50. For example, the first extraction unit 22 may set the intervals at which the plurality of pixels 60 is selected to be shorter as the pixels 60 are farther from the center 70 in an up-and-down direction of the captured image 100.

This focuses on the fact that a water droplet adhered to a lens receives an effect of the gravity. In other words, a water droplet receiving the effect of the gravity has a tendency to have three-dimensional shape obtained by being pulled in a lower direction, and thus the first extraction unit 22 selects the more pixels 60 as the pixels 60 are farther from the center 70 in an up-and-down direction on the basis of this tendency. Thus, the tendency of the water droplet is grasped more strongly, and thus detection accuracy can be improved.

The first extraction unit 22 gradually reduces the interval between the pixels 60 as the pixels 60 are farther from the center 70 in an up-and-down direction, the interval between the pixels 60 may be reduced within a specific range in the up-and-down direction. For example, as illustrated in FIG. 4B, the first extraction unit 22 reduces the interval between the pixels 60 within a predetermined angle β corresponding to the up-and-down direction, and increases the interval between the pixels 60 outside the predetermined angle β. Thus, the pixels 60 can be concentrated in the up-and-down direction, and thus detection accuracy can be more improved.

The first extraction unit 22 may reduce intervals between the pixels 60 with respect to a specific circle among the concentric circles 80. For example, as illustrated in FIG. 4C, the first extraction unit 22 sets the intervals between the pixels 60 of the circle 50b having a predetermined radius W6 to be shorter than those of the circles 50a and 50c. Herein, the radius W6 is, for example, a distance from a center of a water droplet to a boundary between gray-color and black-color regions.

In other words, when the pixels 60 of the circle 50b, which corresponds to a boundary having a comparatively strong tendency to indicate an edge, are set to be more than the pixels 60 of any of the peripheral circles 50a and 50c, the first extraction unit 22 can easily detect a tendency of a water droplet, and thus detection accuracy can be improved.

In FIG. 4C, the intervals between the pixels 60 are reduced with respect to the circle 50b having the predetermined radius W6, the intervals of the pixels 60 can be reduced with respect to a circle existing within predetermined ranges on respective outer-peripheral and inner-peripheral sides while placing midmost, for example, the predetermined radius W6 therebetween. For example, the first extraction unit 22 may set the interval between the pixels 60 to be shorter as a radius is closer to the predetermined radius W6.

Figure 5A:
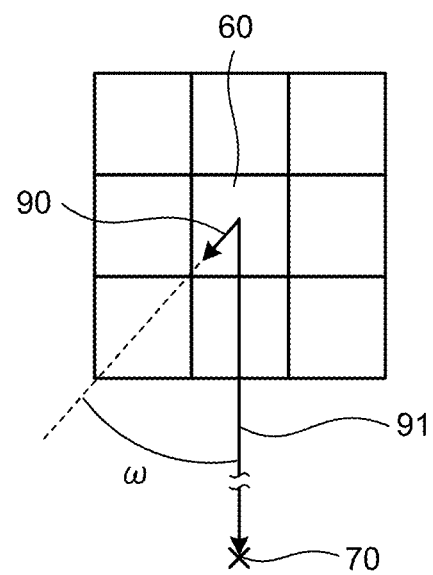
FIGS. 5A to 5B are a diagrams illustrating processing details of the first extraction unit.
Figure 5B:
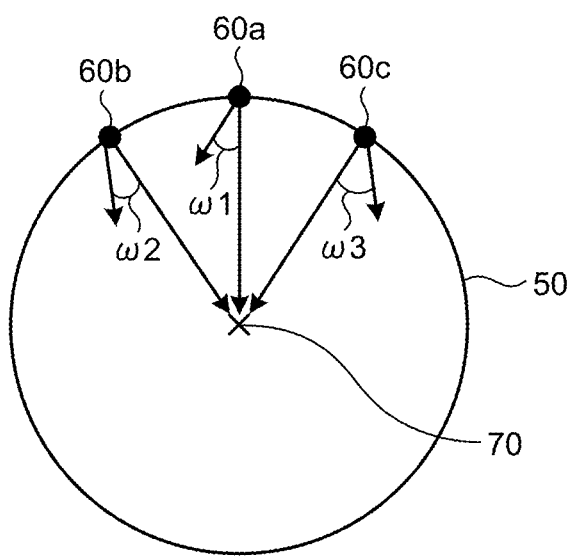

Next, with reference to FIGS. 5A and 5B, processing details of the first extraction unit 22 will be explained. FIGS. 5A and 5B are diagrams illustrating processing details of the first extraction unit 22. In FIG. 5A, the one pixel 60 and pixels arranged around this pixel 60 are schematically illustrated.

The first extraction unit 22 detects the candidate pixel 62 that is a candidate for a pixel of a region that is estimated, from among the plurality of pixels 60, to indicate a water droplet adhered to a lens of the camera 10, on the basis of at least one of an intensity of an edge of the pixel 60 selected by the first extraction unit 22 and an angle ω between a direction of the edge and that toward the center 70 from this pixel 60.

Specifically, the first extraction unit 22 first detects an edge intensity and an edge direction 90 of the pixel 60. The first extraction unit 22 differentiates the luminance and color components of the pixel 60 and the peripheral pixels so as to detect an edge by using a Sobel filter that detects gradients of the luminance and color components.

For example, the first extraction unit 22 detects, as an edge intensity, the largest gradient of the detected gradients of the luminance from the pixel 60 to the peripheral pixels so as to detect a direction of the largest gradient as the edge direction 90. Not limited to the edge detecting method using the Sobel filter, the first extraction unit 22 may use another edge detecting method such as a Laplacian filter.

Next, the first extraction unit 22 computes the angle α between a vector of the detected edge direction 90 and a direction 91 from the pixel 60 toward the pixel of the center 70. A value of this angle ω is closer to any of 0 degrees (direction approaching pixel) or 180 degrees (direction moving away from pixel) as a direction of the gradient of the luminance or the color component is directed to the center pixel more rightly. Thus, extraction accuracy of the candidate pixel 62 can be improved.

The first extraction unit 22 extracts, as the candidate pixel 62, the pixel 60 at least one of whose edge intensity and computed angle ω is within a range between predetermined upper and lower limits.

For example, when the gradient of the luminance or the color component of the pixel 60 is large and the direction of this gradient is within a predetermined angle for the center 70, the first extraction unit 22 detects this pixel 60 as the candidate pixel 62.

In other words, the first extraction unit 22 extracts the candidate pixel 62 by using a tendency, of a water droplet adhered to a lens of the camera 10, to radially spread from the center. Thus, the candidate pixel 62, which is a candidate for a pixel of a water-droplet region, can be detected with high accuracy.

The first extraction unit 22 detects the candidate pixel 62 on the basis of an edge intensity or the angle t of the pixel 60 itself, the first extraction unit 22 may compare, for example, the adjacent pixels 60 so as to detect the candidate pixel 62. This point will be explained with reference to FIG. 5B.

In FIG. 5B, a case will be explained, in which a pixel 60a is detected to be the candidate pixel 62. As illustrated in FIG. 5B, the pixel 60a is adjacent to two pixels 60b and 60c at predetermined intervals while placing the pixel 60a therebetween.

In this case, the first extraction unit 22 extracts from among the plurality of pixels 60, as the candidate pixel 62, the pixels 60a in each of which at least one of: (i) differences between an edge intensity of the pixel 60a and edge intensities of the adjacent pixels 60b and 60c; and (ii) a difference between angles ω1 and ω2 and ω3, and a difference between angles ω1 and ω3 is within a range between predetermined upper and lower limits.

For example, as illustrated in FIG. 5B, when the difference between the angle ω1 of the pixel 60a and the angle ω2 of the pixel 60b and the difference between the angle ω1 and the angle ω3 of the pixel 60c are smaller than an upper-limit threshold, the first extraction unit 22 detects the pixel 60a as the candidate pixel 62.

In other words, the fact is focused on that the pixels 60 existing in a region of a boundary between gray-color and black-color regions are collectively indicate directions of vectors toward the center 70. Thus, the candidate pixel 62 can be extracted with high accuracy.

In FIG. 5B, the first extraction unit 22 compares the pixel 60*a* with the adjacent pixels 60*b* and 60*c* on the same circumference of the circle so as to detect the candidate pixel 62, not limited to the pixels 60*b* and 60*c* on the circumference of the same circle. For example, the first extraction unit 22 may compare the pixel 60*a* with the pixel 60 of a circle on an inner-peripheral side of the circle on which the pixel 60*a* exists and the pixel 60 of a circle on an outer-peripheral side of the circle on which the pixel 60*a* exists so as to detect the candidate pixel 62.

Figure 6A:
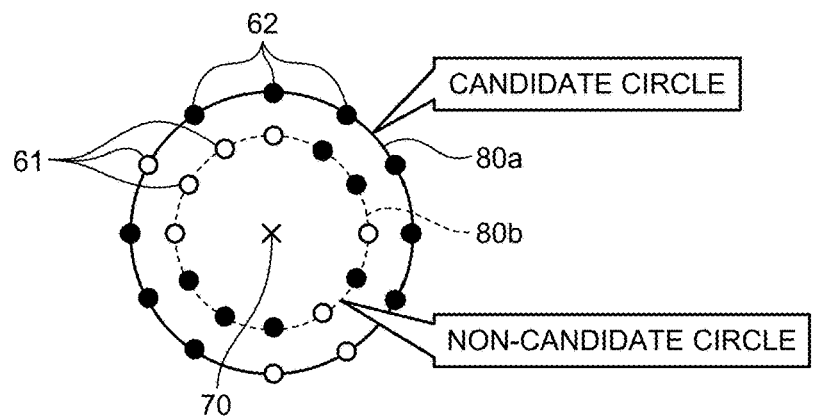
FIGS. 6A to 6C are a diagrams illustrating determination processes to be executed by a second extraction unit.
Figure 6B:
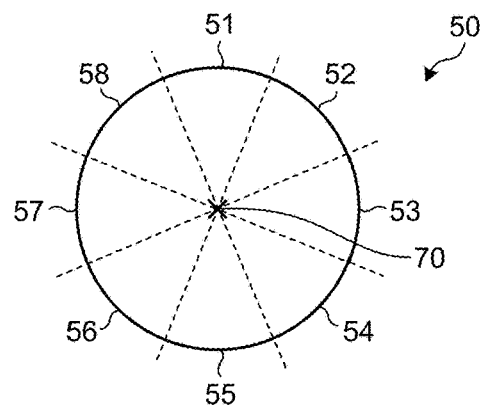
Figure 6C:
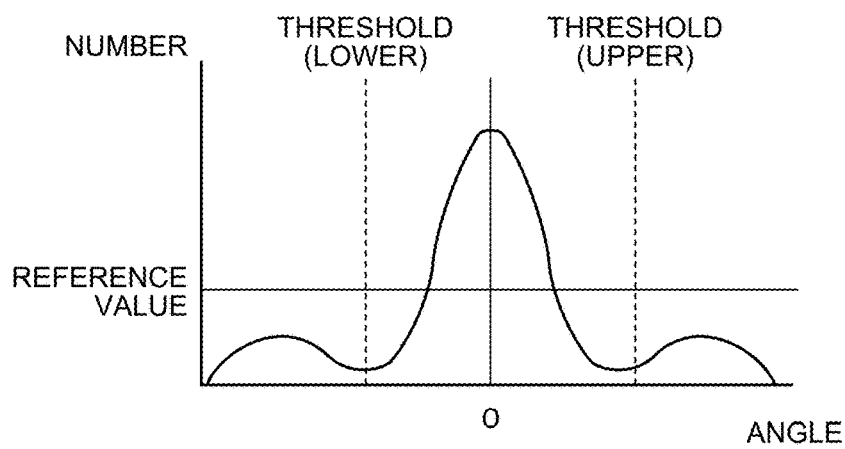

Next, with reference to FIGS. 6A to 6C, a determination process to be executed the second extraction unit 23 will be explained. FIGS. 6A to 6C are diagrams illustrating determination processes to be executed by the second extraction unit 23. In FIG. 6A, the candidate pixels 62 (black circles) and the non-candidate pixels 61 (white circles) not being the candidate pixels 62 are illustrated, which are detected by the first extraction unit 22.

The second extraction unit 23 extracts the candidate circle 80*a*, which is a candidate for a circle indicating a shape of a water droplet, on the basis of the candidate pixels 62 extracted by the first extraction unit 22 and the determination information 31 stored in the storage 3.

Herein, the determination information 31 includes information being a condition for determining whether the circle 50 included in the concentric circles 80 is the candidate circle 80*a* or a non-candidate circle 80*b*, and information being a condition for determining whether or not a region of the concentric circle 80 is a water-droplet region.

For example, as illustrated in FIG. 6A, the second extraction unit 23 extracts from among the circles 50 the concentric circles 80, as the candidate circle 80*a*, the circle 50 on which a predetermined number (in FIG. 6A, "6") of the candidate pixels 62 are sequentially adjacent to one another.

On the other hand, the second extraction unit 23 extracts, as the non-candidate circle 80*b*, the circle 50 on which a predetermined number of the candidate pixel 62 are not sequentially adjacent to one another. Thus, when a circle on which the concentrated candidate pixels 62 exist is set to be the candidate circle 80*a*, extraction accuracy of the candidate circle 80*a* can be improved.

When a predetermined number of the candidate pixels 62 are sequentially adjacent to one another, the second extraction unit 23 extracts the candidate circle 80*a*, not limited thereto. For example, the second extraction unit 23 may extract the candidate circle 80*a* when a predetermined number or more of the candidate pixels 62 are extracted from a circumference of the same circle of the concentric circles 80.

In other words, even when a predetermined number of the candidate pixels 62 are not sequentially adjacent to one another, the second extraction unit 23 extracts, as the candidate circle 80*a*, the circle 50 from which a predetermined number or more of the candidate pixel 62 are extracted. Thus, detection accuracy can be more improved. The second extraction unit 23 may extract the circle 50 as the candidate circle 80*a* when, for example, a ratio of the candidate pixels 62 to the pixels 60 existing on a circumference of the same circle is a predetermined value or more.

The second extraction unit 23 extracts the candidate circle 80*a* on the basis of all of the pixels 60 on a circumference of the same circle, not limited thereto, for example, as illustrated in FIG. 6B, the one circle 50 may be divided into a plurality of arcs 51 to 58 so as to determine whether or not the condition of the determination information 31 is satisfied for each of the divided arcs 51 to 58.

Specifically, the second extraction unit 23 divides the circle 50 of the concentric circles 80 into the plurality of arcs 51 to 58 at predetermined angles, and extracts the candidate circle 80*a* on the basis of distributions of the candidate pixels 62 on the divided arcs 51 to 58.

For example, as illustrated in FIG. 6B, the second extraction unit 23 first divides the one circle 50 of the concentric circles 80 into the plurality of arcs 51 to 58. Next, the second extraction unit 23 determines, in accordance with the determination information 31, whether or not each of the arcs 51 to 58 satisfies a predetermined condition that is, for example, whether or not a predetermined number or more of the candidate pixels 62 are sequentially adjacent to one another, and the like.

For example, when a predetermined number or more of the arcs that satisfy the condition of the determination information 31 exist among the plurality of arcs 51 to 58, the second extraction unit 23 extracts the circle 50 corresponding to these arcs as the candidate circle 80*a*. Thus, for example, even when a tendency toward an edge of a water-droplet region concentrates in one of the arcs, the candidate circle 80*a* can be extracted. When the arc, among the plurality of arcs 51 to 58, in a predetermined position satisfies the condition, the second extraction unit 23 may extract the circle 50 corresponding to this arc as the candidate circle 80*a*.

For example, among the plurality of arcs 51 to 58 illustrated in FIG. 6B, when any one of the two arcs 51 and 55 existing in the up-and-down direction satisfies the condition of the determination information 31, the second extraction unit 23 extracts the circle 50 as the candidate circle 80*a*.

A water droplet adhered to a lens of the camera 10 pulled by the gravity easily indicates a tendency toward an edge in the up-and-down direction, and thus, when the second extraction unit 23 sets only this up-and-down direction to be a determination target, detection accuracy can be improved while reducing a processing load.

In FIG. 6B, the plurality of arcs 51 to 58 are divided at the equal intervals, not limited thereto, a division interval and a division number may be variable for each radius of the circle 50, for example.

The second extraction unit 23 extracts the candidate circle 80*a* on the basis of the number of the candidate pixels 62, however, as illustrated in, for example, FIG. 6C, the edge intensity of the pixel 60 and a unevenness of a degree-number distribution of the angle ω may be considered.

In FIG. 6C, a graph of a degree-number distribution of angles of the pixels 60 on the one circle 50 is illustrated. In this graph, a vertical axis indicates the number of the candidate pixels 62 and the non-candidate pixels 61, and a lateral axis indicates the angle. The lateral axis is not limited to the angle, and may be the edge intensity.

A threshold (upper) and a threshold (lower) illustrated in FIG. 6C indicate respective upper-limit and lower-limit thresholds of whether the pixel 60 is, for example, the candidate pixel 62 or the non-candidate pixel 61. The second extraction unit 23 extracts from among the circles 50 of the concentric circles 80, as the candidate circle 80*a*, the circle 50 at least one of whose unevenness of the edge intensities and unevenness of the angles of the pixels 60 on a circumference of the circle is within a predetermined range.

Herein, "within the predetermined range" indicates the dispersion is equal to or less than, for example, a reference value illustrated in FIG. 6C. In other words, for example, when the number of the pixels 60 whose angles are out of a range between the threshold (upper) and the threshold (lower) is equal to or less than the reference value, the second extraction unit 23 extracts the circle 50 as the candidate circle 80*a*.

In other words, all of the pixels 60 of the selected circle 50 are statistically determined so as to extract the candidate circle 80*a*, and thus extraction accuracy of the candidate circle 80*a* can be stabilized.

Moreover, "within a predetermined range" is not limited to the reference value illustrated in FIG. 6C, and may be, for example, standard deviation. For example, the second extraction unit 23 computes a value of standard deviation from the degree-number distribution table illustrated in FIG. 6C, when the value of standard deviation is equal to or less than a predetermined threshold, in other words, many edges direct toward the center 70, the second extraction unit 23 extracts the candidate circle 80*a*.

Figure 7:
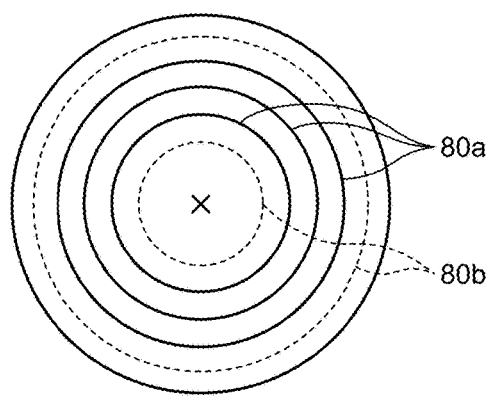
FIGS. 7 to 8 are a diagrams illustrating processes for determining a water droplet to be executed by a determination unit.
Figure 8:
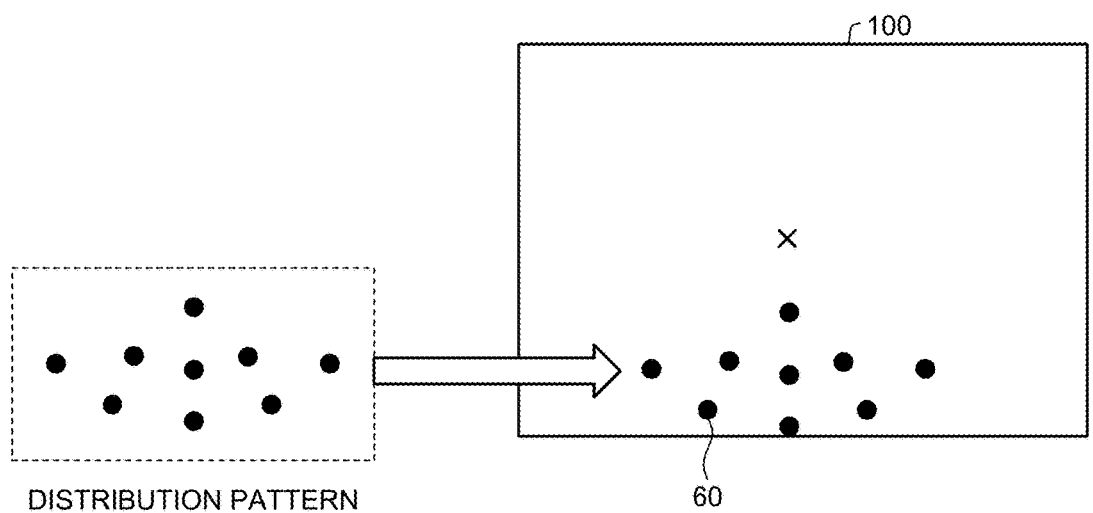

Next, with reference to FIGS. 7 and 8, processes for determining a water droplet to be executed by the determination unit 24 will be explained. FIGS. 7 and 8 are diagrams illustrating processes for determining a water droplet to be executed by the determination unit 24. In FIG. 7, the candidate circles 80*a* and the non-candidate circles 80*b* included in the concentric circles 80 are illustrated.

When the candidate circles 80*a* and the non-candidate circles 80*b* satisfy a predetermined condition, the determination unit 24 determines that a water droplet is adhered. For example, as illustrated in FIG. 7, when a predetermined number (in FIG. 7, "3") or more of the candidate circles 80*a* are adjacent to one another, the determination unit 24 determines that a water droplet is adhered.

In other words, the determination condition of the determination unit 24 is that the candidate circles 80*a* are sequentially adjacent to one another, which is based on a width of a blurred boundary of gray-color and black-color regions. Thus, when the determination is performed on the basis of a shape of a water droplet, adhesion of a water droplet can be detected with high accuracy.

Even in a case where a predetermined number of the candidate circles 80*a* are not sequentially adjacent to one another, when, for example, a ratio of the candidate circles 80*a* to all of the circles of the concentric circles 80 is a predetermined value or more, the determination unit 24 may determine that a water droplet is adhered.

The determination unit 24 may consider the non-candidate circle 80*b* in addition to the candidate circle 80*a*. Specifically, when the candidate circle 80*a* is adjacent to the non-candidate circles 80*b* (not candidate circles 80*a*) on respective inner-peripheral and outer-peripheral sides, the determination unit 24 determines that a water droplet is adhered.

In other words, when the non-candidate circle 80*b*, the candidate circle 80*a*, and the non-candidate circle 80*b* are sequentially arranged in a belt-like shape from the center of the concentric circles 80, the determination unit 24 detects adhesion of a water droplet.

Thus, for example, even when edge directions of the pixels 60 are, due to a background with little undulation such as a wall and an angle of the sunlight, toward the center 70 in a wide range of the captured image 100, a water droplet can be detected with high accuracy.

The determination unit 24 may focus on a gray-color region, in which an edge intensity is weak, so as to determine adhesion of a water droplet. Specifically, when, among the circles 50 of the concentric circles 80, a predetermined number or more of circles having weak edge intensities are adjacent to one another within a predetermined distance from the center 70, the determination unit 24 determines that a water droplet is adhered.

For example, the second extraction unit 23 extracts from among the concentric circles 80, as a circle with a weak-edge intensity (weak-gradient intensity), the circle 50 having, on a circumference of the circle, a predetermined number or more of the candidate pixels 62 whose edge intensities are equal to or less than a predetermined threshold. The pixel on the circumference of the circle is not limited to the candidate pixel 62, and it is sufficient that the pixel is on the circumference of the circle. In other words, when adhesion of a water droplet is detected on the basis of the fact that a plurality of circles having weak edge intensities exists in a region of a gray-color region, detection accuracy of a water droplet can be improved.

When, for example, the candidate circle 80*a* does not exist and only the non-candidate circle 80*b* exists in the concentric circles 80, the determination unit 24 may determine adhesion of a water droplet on the basis of, for example, a distribution pattern of the candidate pixels 62. This point will be explained with reference to FIG. 8.

Specifically, when a distribution of the candidate pixels 62 extracted by the first extraction unit 22 coincides with a predetermined distribution pattern of the candidate pixels 62, the determination unit 24 determines that a water droplet is adhered.

For example, the determination unit 24 stores the distribution pattern illustrated in FIG. 8 in the storage 3, performs pattern matching using this distribution pattern on the captured image 100 so as to compute a coincidence degree indicating how much this distribution pattern coincides with the distribution of the candidate pixels 62, when this coincidence degree is equal to or more than a predetermined value, determines that a distribution pattern exists so as to determine that a water droplet is adhered.

Thus, for example, even in a case where the candidate circle 80*a* is not extracted when a water droplet is not circle-shaped, the water droplet can be detect on the basis of a tendency of a water droplet, so that it is possible to detect a water droplet with high accuracy.

The determination unit 24 determines an object, such as a road sign, whose edge tendency is obviously different from that of a water droplet not to be a water droplet. This point will be explained with reference to FIG. 9.

Figure 9:
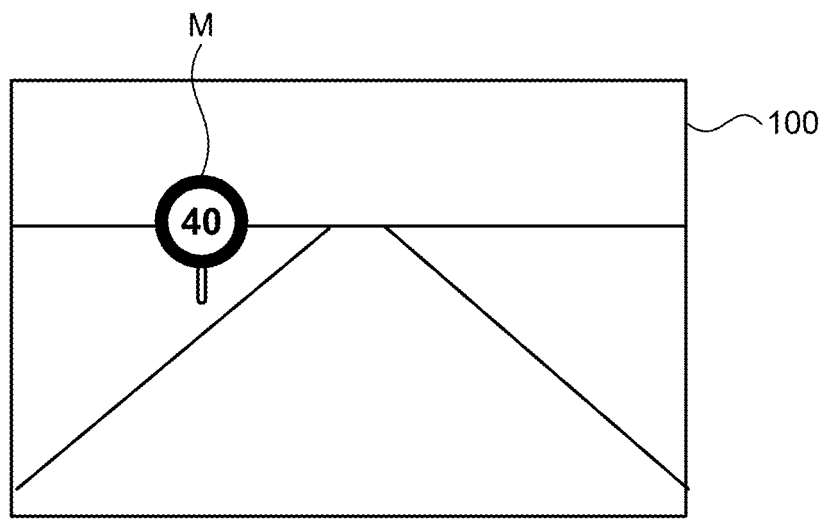
FIG. 9 is a diagram illustrating a process for determining a circle-shaped object other than a water droplet to be executed by the determination unit.

FIG. 9 is a diagram illustrating a process for determining a circle-shaped object other than a water droplet to be executed by the determination unit 24. In FIG. 9, the captured image 100 including, for example, a road sign M existing in front of a vehicle is illustrated. For example, when the road sign M exists in a position that is comparatively far from the vehicle, a profile of the road sign M in the captured image 100 is more or less blurred in some cases.

Thus, there exists a fear that the circle-shaped profile of the road sign M is extracted as the candidate circle 80*a* and adhesion of a water droplet is erroneously determined. Therefore, in a case where a water droplet is determined to be adhered, when an area ratio of a pixel region having a color and a luminance within a predetermined range to an image region corresponding to the water droplet is equal to or more than a predetermined value, the determination unit 24 determines again that the water droplet is not adhered.

When a predetermined number or more of the candidate pixels 62 exist, whose Red-Green-Blue (RGB) values (color components) are those indicating, for example, red, blue, and white, the determination unit 24 determines that a water droplet is not adhered. Alternatively, the determination unit 24 may except this region from a determination target on the basis of the RGB value.

Thus, the determination unit 24 can be prevented from detecting a road sign and the like as a water droplet, and thus determination accuracy of a water droplet can be improved. For example, when the candidate pixels 62 of red, blue, and white have a predetermined area, the determination unit 24 may determine that a water droplet is not adhered.

Next, with reference to FIG. 10, a processing procedure of the detection process to be executed by the water-droplet detecting apparatus 1 according to the embodiment will be explained. FIG. 10 is a flowchart illustrating the processing procedure of the detection process to be executed by the water-droplet detecting apparatus 1 according to the embodiment.

As illustrated in FIG. 10, first, the setting unit 21 specifies a predetermined pixel (Step S101). Next, the setting unit 21 sets the concentric circles 80 having a center of the specified pixel as the center 70 (Step S102).

Next, the first extraction unit 22 extracts the candidate pixels 62 that is candidates for pixels estimated to indicate a water droplet adhered to a lens of the camera 10 on the basis of edge intensities and angles of pixels on a circumference of each of the concentric circles 80 set by the setting unit 21 (Step S103).

Next, the second extraction unit 23 extracts the candidate circle 80a, which is a candidate for a circle indicating a shape of a water droplet, on the basis of the candidate pixels 62 extracted by the first extraction unit 22. Specifically, the second extraction unit 23 determines whether or not the candidate pixels 62 on the circumference of the circle satisfy a predetermined condition (Step S104).

When the candidate pixels 62 on the circumference of the circle satisfy the predetermined condition (Step S104: Yes), the second extraction unit 23 extracts the corresponding circle 50 as the candidate circle 80a (Step S105).

Next, the second extraction unit 23 determines whether or not the determination process for extracting the candidate circle 80a is executed on all of the circles 50 of the concentric circles 80 (Step S106). When the determination process is executed on all of the circles 50 of the concentric circles 80 (Step S106: Yes), the determination unit 24 determines whether or not the extracted candidate circles 80a and the non-candidate circles 80b satisfy a predetermined condition (Step S107).

When the candidate circles 80a and the non-candidate circles 80b satisfy the predetermined condition (Step S107: Yes), the determination unit 24 determines that a water droplet is adhered (Step S108), and terminates the detection process.

On the other hand, in a determination process of Step S104, the candidate pixels 62 on the circumference of the circle do not satisfy the predetermined condition (Step S104: No), the second extraction unit 23 extracts the corresponding circle 50 as the non-candidate circle 80b (Step S109).

In the determination process of Step S106, when the determination process is not executed on all of the circles 50 of the concentric circles 80 (Step S106: No), the determination unit 24 shifts the process to Step S103.

In the determination process of Step S107, when the candidate circles 80a and the non-candidate circles 80b do not satisfy the predetermined condition (Step S107: No), the determination unit 24 shifts the process to Step S101.

As described above, the water-droplet detecting apparatus 1 according to the embodiment includes the setting unit 21, the first extraction unit 22, the second extraction unit 23, and the determination unit 24. The setting unit 21 sets the concentric circles 80 having the center 70 at arbitrary one point of the captured image 100 of an image capturing unit (the camera 10). The first extraction unit 22 extracts the candidate pixels 62 on the basis of gradients of the pixels 60 on a circumference of each of the concentric circles 80 set by the setting unit 21. The candidate pixels 62 are candidates for pixels that are estimated to indicate a water droplet adhered to the image capturing unit. The second extraction unit 23 extracts the one or more candidate circles 80a on the basis of the candidate pixels 62 extracted by the first extraction unit 22. The one or more candidate circles 80a are candidates for circles that indicate a shape of the water droplet. The determination unit 24 determines whether or not the water droplet is adhered on the basis of an extraction result of the second extraction unit 23. Thus, the water droplet can be detected with high accuracy while reducing a processing load.

In the aforementioned embodiment, the setting unit 21 sets the concentric circles 80 without changing a resolution of the captured image 100, for example, the setting unit 21 may reduce the resolution of the captured image 100 and then set the concentric circles 80.

Specifically, when acquiring the captured image 100 from the camera 10, the setting unit 21 first reduces the resolution of the captured image 100 so as to generate a reduced image obtained by reducing an image size of the captured image 100 by a factor of "1/n." Next, the setting unit 21 sets the concentric circles 80 having a center of arbitrary one point of the generated reduced image.

In other words, the setting unit 21 reduces the resolution of the captured image 100 to reduce the number of pixels to be the center 70. Therefore, the number of the concentric circles 80 to be set in one frame of the captured image 100 can be reduced, and thus a processing load can be reduced.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A liquid-droplet detecting apparatus comprising:
a processor programmed to:
set concentric circles having a center at arbitrary one point of a captured image captured by a camera including an image sensor;
extract, as candidates for pixels that indicate a liquid droplet being in contact with the camera, candidate pixels based on gradients of pixels on a circumference of each of the set;
extract, as candidates for circles that indicate a shape of the liquid droplet, one or more candidate circles based on the extracted candidate pixels; and
determine whether or not the liquid droplet is in contact with the camera based on an extraction result of the one or more candidate circles.

2. The liquid-droplet detecting apparatus according to claim 1, wherein
the processor is further programmed to:
extract the candidate pixels based on at least one of: (i) intensities of the gradients of the pixels on the circumference of each of the concentric circles; and (ii) angles between directions of the gradients and respective directions toward the center of the concentric circles from the pixels on the circumference of each of the concentric circles.

3. The liquid-droplet detecting apparatus according to claim 1, wherein
the processor is further programmed to:
preferentially arrange the center of the concentric circles in a central region of the captured image.

4. The liquid-droplet detecting apparatus according to claim 1, wherein
the processor is further programmed to:
provide an extension region obtained by extending the captured image to an outer peripheral side to be able to arrange the center of the concentric circle in the extension region.

5. The liquid-droplet detecting apparatus according to claim 1, wherein
the processor is further programmed to:
when moving the concentric circles, set a position having an interval by at least one pixel from the center of the concentric circles to be a new center of the concentric circles.

6. The liquid-droplet detecting apparatus according to claim 1, wherein
the processor is further programmed not to:
arrange the concentric circles in a region within a predetermined radius from the center of the concentric circles so that the region is not a target for extracting the candidate pixels.

7. The liquid-droplet detecting apparatus according to claim 1, wherein
the processor is further programmed to:
set, within a predetermined range that is estimated to correspond to an outer periphery of the liquid droplet, intervals between the circumferences of the concentric circles to be shorter than those outside the predetermined range.

8. The liquid-droplet detecting apparatus according to claim 1, wherein
the processor is further programmed to:
extract the candidate pixels from among a plurality of pixels that is selected at predetermined intervals from among the pixels on the circumference of each of the concentric circles.

9. The liquid-droplet detecting apparatus according to claim 8, wherein
the processor is further programmed to:
vary the intervals at which the plurality of pixels is selected in accordance with a radius of the circumference of each of the concentric circles.

10. The liquid-droplet detecting apparatus according to claim 8, wherein
the processor is further programmed to:
set the intervals, at which the plurality of pixels is selected, to be shorter as the pixels are farther from the center of the concentric circles in an up-and-down direction of the captured image.

11. The liquid-droplet detecting apparatus according to claim 8, wherein
the processor is further programmed to:
extract from among the plurality of pixels, as the candidate pixel, a pixel in which at least one of: (i) an intensity of the gradient; and (ii) an angle between a direction of the gradient and a direction toward the center of the concentric circles from the pixel is within a range from a predetermined lower limit to a predetermined upper limit.

12. The liquid-droplet detecting apparatus according to claim 8, wherein
the processor is further programmed to:
extract from among the plurality of pixels, as the candidate pixels, pixels in each of which at least one of: (i) a difference between intensities of gradients of the pixel and an adjacent pixel adjacent to the pixel; and (ii) a difference between an angle between a direction of the gradient of the pixel and a direction toward the center of the concentric circles from the pixel and an angle between a direction of the gradient of the adjacent pixel and a direction toward the center of the concentric circles from the adjacent pixel is within a range from a predetermined lower limit to a predetermined upper limit.

13. The liquid-droplet detecting apparatus according to claim 1, wherein
the processor is further programmed to:
extract from among the concentric circles, as the one or more candidate circles, one or more circles from each of which a predetermined number or more of the candidate pixels are extracted.

14. The liquid-droplet detecting apparatus according to claim 1, wherein
the processor is further programmed to:
extract from among the concentric circles, as the one or more candidate circles, one or more circles on each of which a predetermined number or more of the candidate pixels sequentially exist.

15. The liquid-droplet detecting apparatus according to claim 1, wherein
the processor is further programmed to:
divide the circumference of each of the concentric circles into a plurality of arcs at predetermined angles, and extracts the one or more candidate circles based on a distribution of the candidate pixels on each of the divided arcs.

16. The liquid-droplet detecting apparatus according to claim 1, wherein
the processor is further programmed to:
extract from among the concentric circles, as the one or more candidate circles, one or more circles in each of which at least one of: (i) an unevenness of intensities of gradients of pixels on a circumference of the corresponding circle; and (ii) an unevenness of angles between directions of the gradients and respective directions toward the center of the concentric circles from the pixels on the circumference is within a predetermined range.

17. The liquid-droplet detecting apparatus according to claim 1, wherein
the processor is further programmed to:
determine that the liquid droplet is in contact with the camera when a predetermined number or more of the candidate circles are sequentially adjacent to one another.

18. The liquid-droplet detecting apparatus according to claim 1, wherein
the processor is further programmed to:
determine that the liquid droplet is in contact with the camera when one of the candidate circles adjacent to non-candidate circles that are not the candidate circle on inner-peripheral and outer peripheral sides of the one candidate circle.

19. A liquid-droplet detecting method comprising:
setting concentric circles having a center at arbitrary one point of a captured image captured by a camera including an image sensor;
extracting, as candidates for pixels that indicate a liquid droplet being in contact with the camera, candidate pixels based on gradients of pixels on a circumference of each of the set concentric circles;

extracting, as candidates for circles that indicate a shape of the liquid droplet, one or more candidate circles based on the extracted candidate pixels; and determining whether or not the liquid droplet is in contact with the camera based on an extraction result.

20. A non-transitory computer-readable recording medium having stored therein a program that causes a computer to execute a process comprising:

setting concentric circles having a center at arbitrary one point of a captured image captured by a camera including an image sensor;

extracting, as candidates for pixels that indicate a liquid droplet being in contact with the camera, candidate pixels based on gradients of pixels on a circumference of each of the set concentric circles;

extracting, as candidates for circles that indicate a shape of the liquid droplet, one or more candidate circles based on the extracted candidate pixels; and determining whether or not the liquid droplet is in contact with the camera based on an extraction result.

* * * * *